(12) United States Patent
Yamashita

(10) Patent No.: US 11,045,161 B2
(45) Date of Patent: Jun. 29, 2021

(54) RADIOGRAPHIC IMAGE PROCESSING APPARATUS, RADIOGRAPHIC IMAGE PROCESSING METHOD, AND STORAGE MEDIUM

(71) Applicant: CANON KABUSHIKI KAISHA, Tokyo (JP)

(72) Inventor: Hironori Yamashita, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 75 days.

(21) Appl. No.: 16/374,570

(22) Filed: Apr. 3, 2019

(65) Prior Publication Data

US 2019/0307411 A1 Oct. 10, 2019

(30) Foreign Application Priority Data

Apr. 6, 2018 (JP) .............................. JP2018-074012

(51) Int. Cl.
*G06K 9/00* (2006.01)
*A61B 6/00* (2006.01)
*G06T 7/60* (2017.01)
*G06T 7/00* (2017.01)

(52) U.S. Cl.
CPC ............ *A61B 6/5211* (2013.01); *A61B 6/461* (2013.01); *G06T 7/0012* (2013.01); *G06T 7/60* (2013.01); *G06T 2207/10116* (2013.01); *G06T 2207/30004* (2013.01)

(58) Field of Classification Search
CPC ....... A61B 6/524; A61B 6/461; A61B 6/5211; G06T 7/60; G06T 7/0012; G06T 5/40; G06T 5/001; G06T 2207/10116; G06T 2207/30004
See application file for complete search history.

(56) References Cited

U.S. PATENT DOCUMENTS

| 4,311,911 | A  | * | 1/1982 | Krumme | A61B 6/06 378/11 |
| 6,604,855 | B2 | * | 8/2003 | Katoh | A61B 6/02 378/196 |
| 7,031,429 | B2 | * | 4/2006 | Akagi | A61B 6/463 378/165 |
| 7,298,815 | B2 | * | 11/2007 | Yoshino | G01N 23/046 378/25 |
| 7,502,439 | B2 | * | 3/2009 | Horiuchi | A61B 6/032 378/16 |
| 7,986,767 | B2 | * | 7/2011 | Oogami | G16H 40/63 378/62 |
| 8,199,880 | B2 | * | 6/2012 | Yamada | A61B 6/542 378/114 |

(Continued)

FOREIGN PATENT DOCUMENTS

JP 2014-117306 A 6/2014

*Primary Examiner* — Amir Alavi
(74) *Attorney, Agent, or Firm* — Canon U.S.A., Inc. IP Division

(57) ABSTRACT

A radiographic image processing apparatus includes a specifying unit that specifies an irradiation field region in a radiographic image, a determination unit that determines, based on the irradiation field region, a rotation angle of the radiographic image, a rotation unit that rotates, based on the determined rotation angle, the radiographic image, and a display control unit that performs control to display the rotated radiographic image on a display unit.

20 Claims, 10 Drawing Sheets

(56) References Cited

U.S. PATENT DOCUMENTS

| | | | | |
|---|---|---|---|---|
| 8,385,623 B2* | 2/2013 | Sakai | ...................... | A61B 6/589 |
| | | | | 382/132 |
| 10,373,350 B2* | 8/2019 | Ye | ......................... | G06T 11/006 |
| 2003/0031291 A1* | 2/2003 | Yamamoto | ........... | A61B 6/0487 |
| | | | | 378/41 |
| 2010/0080436 A1* | 4/2010 | Ohara | .................. | A61B 6/4291 |
| | | | | 382/132 |
| 2019/0307411 A1* | 10/2019 | Yamashita | ................ | G06T 7/60 |

* cited by examiner

FIG.7

| ROTATION ANGLE | IMAGE QUALITY DETERIORATION RATIO (%) |
|---|---|
| 0 | 0 |
| 1 | 2.0 |
| 2 | 2.2 |
| 3 | 2.2 |
| 4 | 2.4 |
| ~ | ~ |
| 15 | 2.5 |
| ~ | ~ |
| 31 | 1.9 |
| ~ | ~ |
| 90 | 0 |
| ~ | ~ |
| 359 | 2.0 |

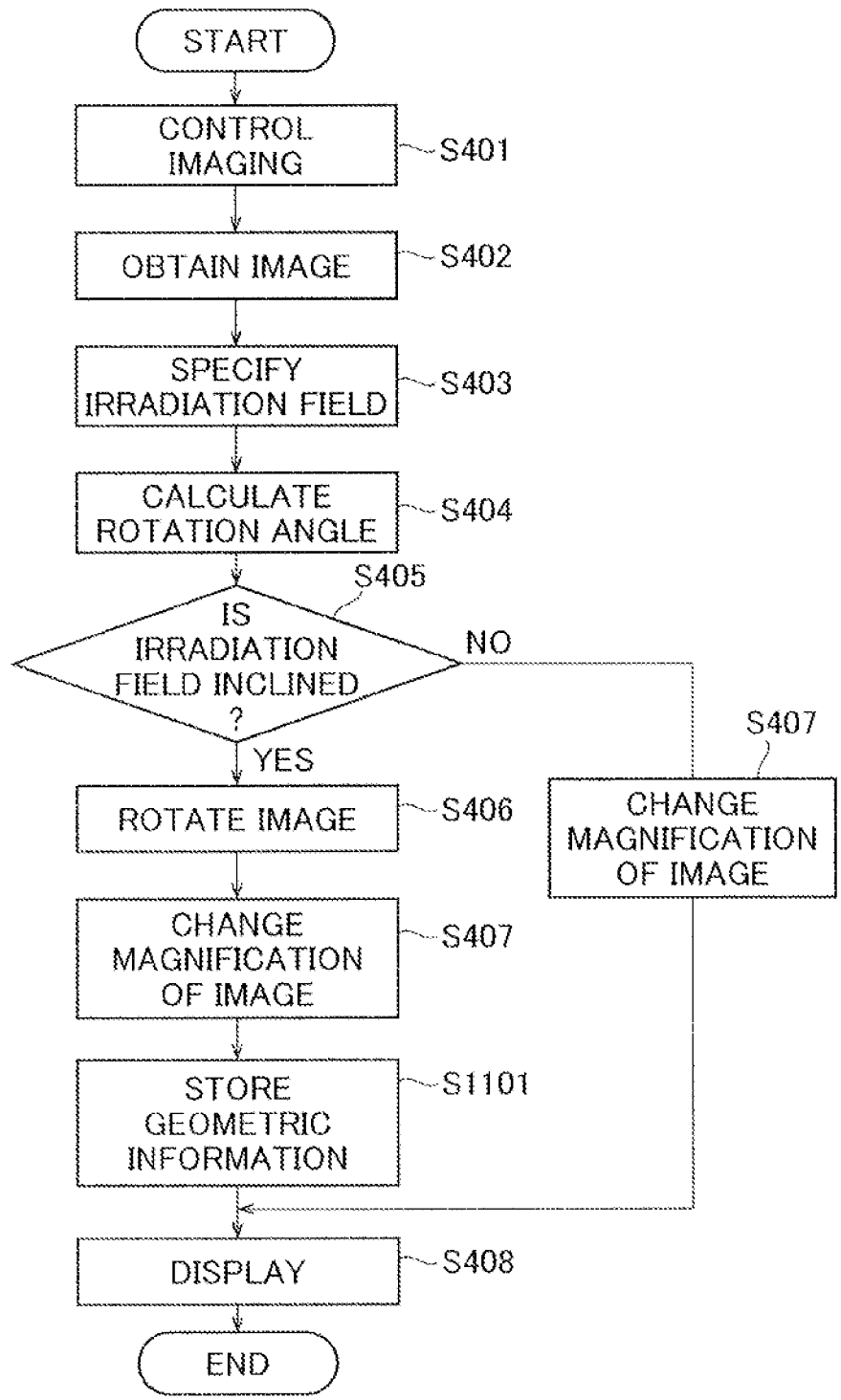

RADIOGRAPHIC IMAGE PROCESSING APPARATUS, RADIOGRAPHIC IMAGE PROCESSING METHOD, AND STORAGE MEDIUM

BACKGROUND

Field

The present disclosure relates to a radiographic image processing apparatus, a radiographic image processing method, and a storage medium.

Description of the Related Art

In recent years, there is a tendency to capture images of all diagnosis target portions by an X-ray detector of single size, such as a large flat panel detector (FPD), in comparatively small medical facilities and the like. When an image of a diagnosis target portion that is small relative to the X-ray detector is to be captured, an irradiation field is typically limited so that only a required region is irradiated with radiation to suppress exposure to radiation in regions other than the required region.

A known technique includes displaying on a display unit an image of only an irradiated portion obtained by limiting an irradiation field as a diagnosis image at a time of diagnosis. Japanese Patent Laid-Open No. 2014-117306 discloses a technique of generating an irradiation field inclusive region of a smallest size that includes an irradiation field region limited by the irradiation field limitation and displaying, in an enlarged manner, an image of the irradiation field inclusive region in a display device of a radiographic apparatus. In the technique of Japanese Patent Laid-Open No. 2014-117306, if the irradiation field region in a radiographic image is inclined due to imaging being performed while an irradiation field is diagonally set relative to the X-ray detector, a rectangular irradiation field inclusive region of a smallest size that includes the irradiation field is displayed in an enlarged manner.

In the case where the irradiation field inclusive region is displayed in the enlarged manner as described above, a large region other than the irradiation field region can be included. Therefore, there arises a problem that operations including rotation of an image and a change of a magnification of an image are required to be performed by an operator so that an image suitable for the diagnosis is displayed.

SUMMARY

An aspect of the present disclosure provides appropriate display of an image including an irradiation field region.

According to an aspect of the present disclosure, a radiographic image processing apparatus includes a specifying unit configured to specify an irradiation field region in a radiographic image, a determination unit configured to determine, based on the irradiation field region, a rotation angle of the radiographic image, a rotation unit configured to rotate, based on the determined rotation angle, the radiographic image, and a display control unit configured to perform control to display a rotated radiographic image on a display unit.

According to another aspect of the present disclosure, a radiographic image processing method of a radiographic image processing apparatus, the method includes specifying an irradiation field region in a radiographic image, determining, based on the irradiation field region, a rotation angle of the radiographic image, rotating, based on the determined rotation angle, the radiographic image, and performing control to display a rotated radiographic image on a display unit.

Further features will become apparent from the following description of exemplary embodiments with reference to the attached drawings.

BRIEF DESCRIPTION OF THE DRAWINGS

FIG. 7 is a diagram illustrating an example of a deterioration ratio table.

FIG. 11 is a flowchart of radiographic image processing.

DESCRIPTION OF THE EMBODIMENTS

Hereinafter, embodiments of the present disclosure will be described with reference to the accompanying drawings.

First Embodiment

Figure 1:
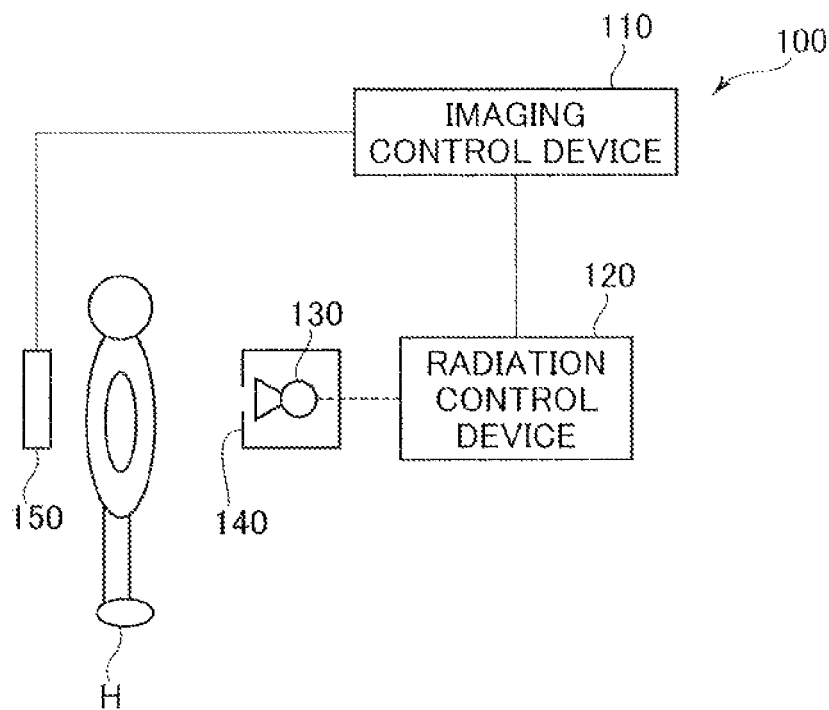
FIG. 1 is a diagram illustrating a radiographic system.

FIG. 1 is a diagram illustrating a radiographic system 100. Here, radiation is not limited to an X-ray, but can include an α ray, a β ray, a γ ray, a particle ray, and a cosmic ray. The radiographic system 100 includes an imaging control device 110, a radiation control device 120, a radiation source (radiation generation unit) 130 that generates radiation, a collimator 140 that limits an irradiation range of radiation, and a radiation detection unit 150.

The imaging control device 110 controls radiography. The imaging control device 110 performs image processing and the like on a radiographic image obtained by the radiation detection unit 150. The radiation control device 120 controls irradiation of radiation performed by the radiation source 130 and controls an irradiation range determined by the collimator 140. The radiation detection unit 150 detects radiation that is emitted from the radiation source 130 and transmitted through a certain portion of a subject H and obtains a radiographic image based on the detected radiation. The radiation detection unit 150 is, for example, a flat panel detector (FPD) to detect X-rays.

Figure 2:
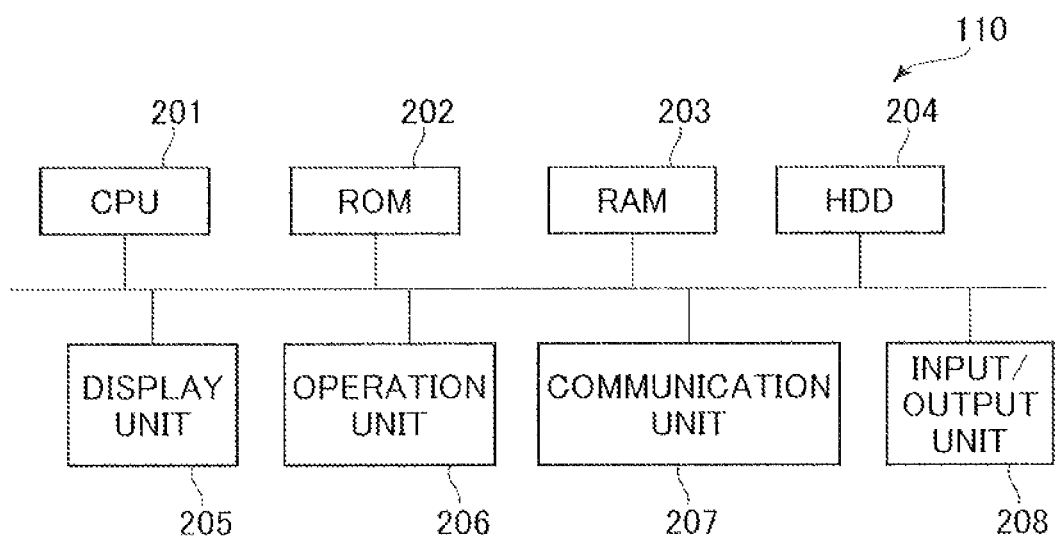
FIG. 2 is a diagram illustrating a hardware configuration of an imaging control device.

FIG. 2 is a diagram illustrating a hardware configuration of the imaging control device 110. The imaging control device 110 includes a central processing unit (CPU) 201, a read only memory (ROM) 202, a random access memory (RAM) 203, a hard disk drive (HDD) 204, a display unit 205, an operation unit 206, a communication unit 207, and an input/output unit 208. The CPU 201 reads control programs stored in the ROM 202 and executes various processes. The RAM 203 is used as a main memory of the CPU 201 and a temporary storage region, such as a work area. The HDD 204 stores various data, various programs, and the like.

The display unit 205 displays various information. The display unit 205 displays an image, such as a radiographic image obtained by the radiation detection unit 150, for example. The operation unit 206 includes a keyboard and a mouse and accepts various operations performed by a user. The operation unit 206 supplies operation information for performing operations of processes in the radiographic system 100 to the imaging control device 110 in response to inputs by an operator (e.g., a radiography engineer or a doctor).

The display unit 205 displays various graphics each indicating timings of a sequence of the radiographic system 100 for the operator. The display unit 205 displays, for example, graphical user interfaces (GUIs) of control software of the radiography. The operation unit 206 supplies operation information to the imaging control device 110 as a result of an image operation having been performed with use of the input device, such as a mouse or a keyboard, on various graphics and image regions displayed in the display unit 205. The display unit 205 and the operation unit 206 can be integrally formed as a touch-panel display or the like.

The communication unit 207 performs a process of communicating with an external apparatus via a network. The communication unit 207 communicates with a server apparatus or the like that mainly performs image management. The server apparatus can be realized, for example, by a picture archiving and communication systems (PACS) that manages radiographic images. The input/output unit 208 performs input of a radiographic image from the radiation detection unit 150 and an output of a control signal to the radiation control device 120.

Functions and processes by the imaging control device 110 described below are realized when the CPU 201 reads programs stored in the ROM 202 or the HDD 204 and executes the read programs. As another example, the CPU 201 can read programs stored in a recording medium, such as a secure digital (SD) card, instead of the ROM 202 or the like.

In another example, at least part of the functions and processes of the imaging control device 110 can be realized by operating a plurality of CPUs, RAMs, ROMs, and the storages in combination. In yet another, at least part of the functions and processes of the imaging control device 110 can be realized using a hardware circuit. The imaging control device 110 can be installed in a fixed manner in a laboratory, or the imaging control device 110 can be realized as a movable system, such as a car.

Figure 3:
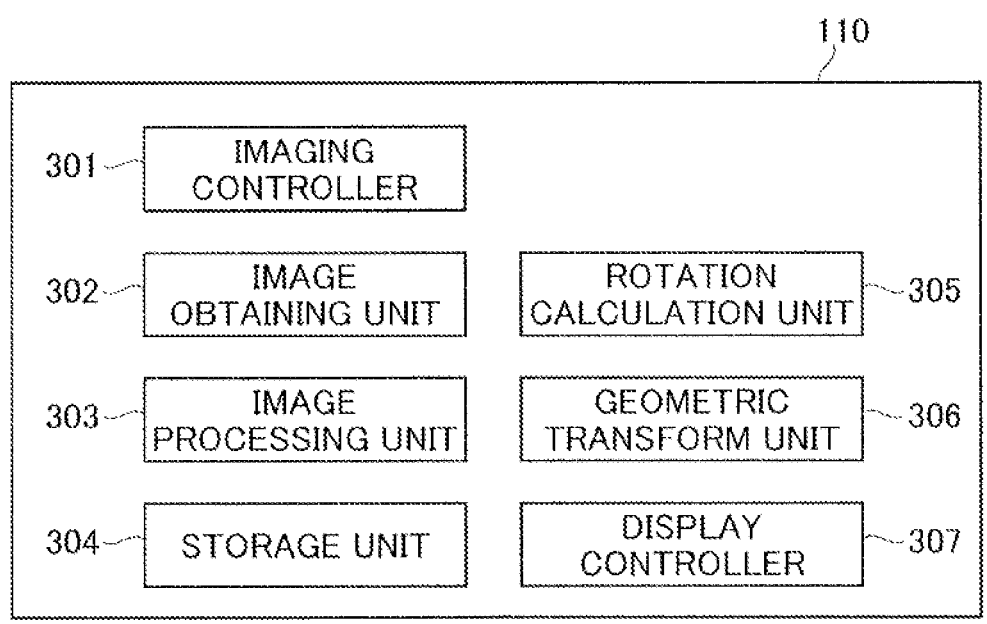
FIG. 3 is a diagram illustrating a functional configuration of the imaging control device.

FIG. 3 is a diagram illustrating a functional configuration of the imaging control device 110. The imaging control device 110 includes an imaging controller 301, an image obtaining unit 302, an image processing unit 303, a storage unit 304, a rotation calculation unit 305, a geometric transform unit 306, and a display controller 307. The imaging controller 301 issues an instruction for performing radiography via the input/output unit 208. The image obtaining unit 302 obtains a radiographic image obtained under control of the imaging controller 301 via the input/output unit 208.

The image processing unit 303 performs feature analysis on a radiographic image and performs gradation conversion and a dynamic range compression process that are suitable for an imaging portion to generate an image having appropriate luminance and appropriate contrast. The image processing unit 303 also performs calculation on an irradiation field region in the radiographic image using a result of the feature analysis. The image processing unit 303 stores a radiographic image and irradiation field information indicating an irradiation field in the storage unit 304. Note that, in the imaging control device 110 of the first embodiment, the image processing unit 303 is realized by the CPU 201. However, as another example, hardware, such as a CPU, which performs image processing may be provided separately from the CPU 201 that controls the entire imaging control device 110 and the hardware may realize the image processing unit 303.

The rotation calculation unit 305 calculates a rotation angle associated with a rotation process serving as a process of displaying the irradiation field region based on the geometric positional relationship between the irradiation field region and a radiographic image. The geometric transform unit 306 performs geometric transform on the radiographic image including the irradiation field region. Specifically, the geometric transform unit 306 rotates the radiographic image including the irradiation field region based on the rotation angle calculated by the rotation calculation unit 305 and changes a magnification of the radiographic image in accordance with a display size of the display unit 205. The change of a magnification includes size reduction and size enlargement. The geometric transform processing also includes transform by parallel shift, for example. The display controller 307 performs control such that the radiographic image that has been subjected to the geometric transform is displayed in the display unit 205.

Figure 4:
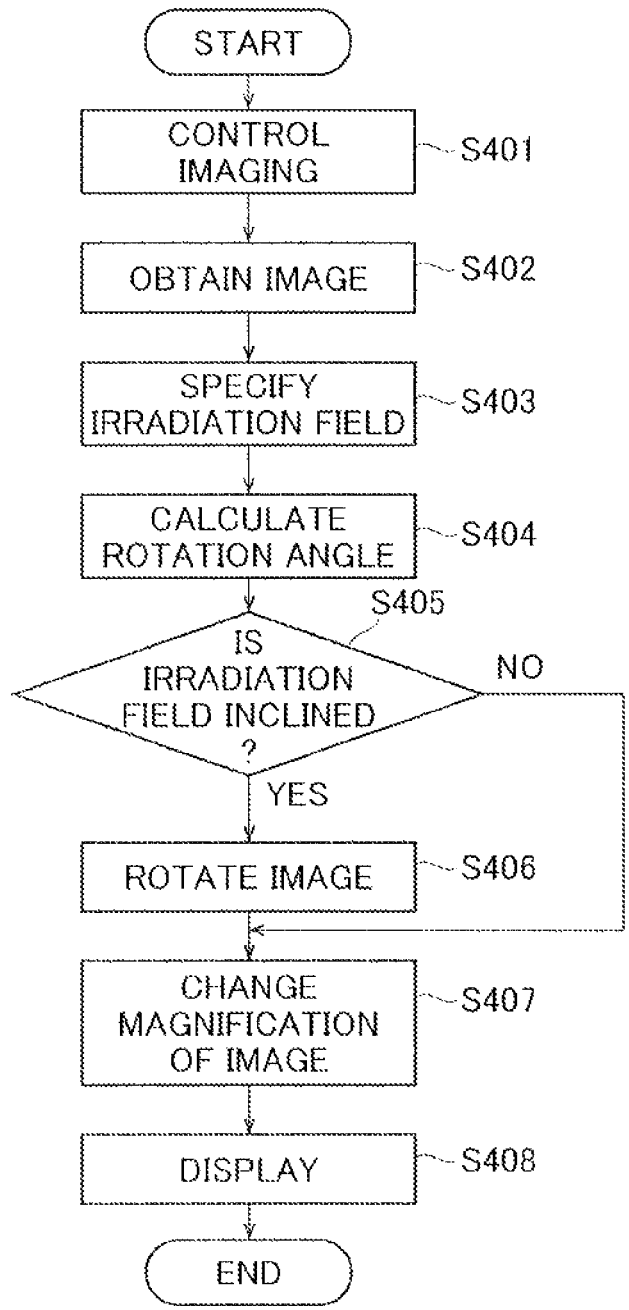
FIG. 4 is a flowchart of radiographic image processing.
Figure 5:
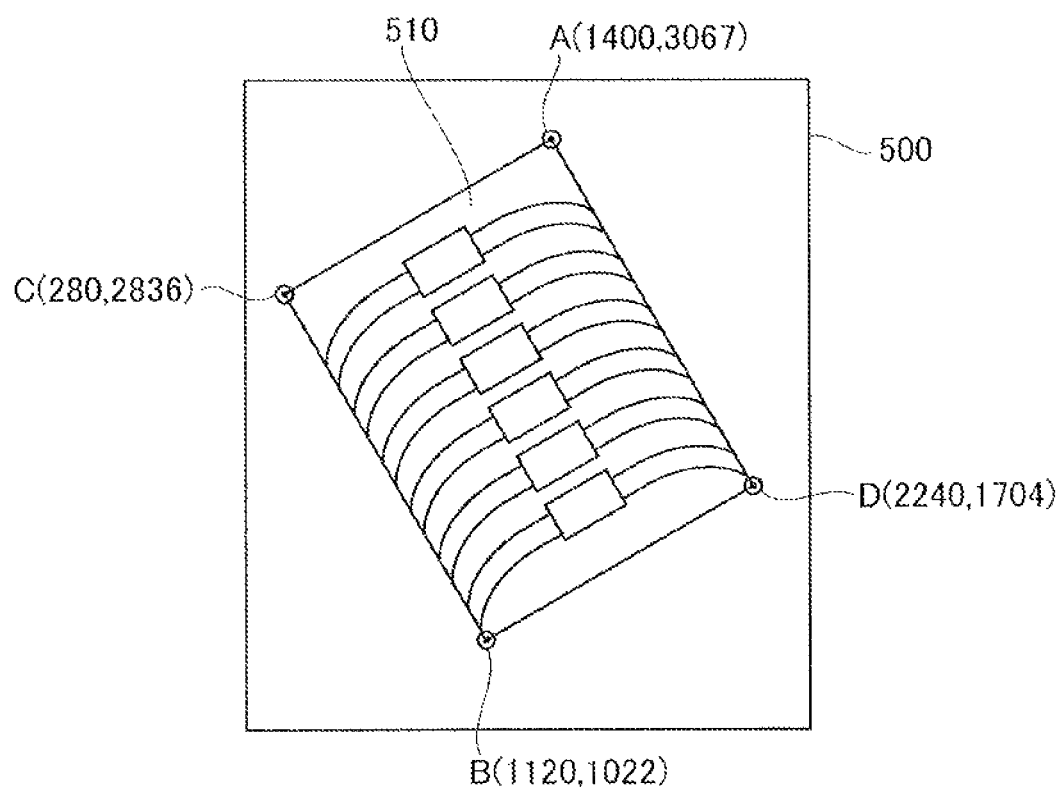
FIG. 5 is a diagram illustrating an example of a radiographic image.

FIG. 4 is a flowchart of radiographic image processing performed by the imaging control device 110. FIG. 5 is a diagram illustrating an example of a radiographic image obtained by the image obtaining unit 302. Here, the radiographic image processing will be described for a case where the image obtaining unit 302 obtains a radiographic image 500 illustrated in FIG. 5 as an example. In step S401, the imaging controller 301 executes control of radiography. Specifically, when an instruction for executing radiography is input through the operation unit 206, the imaging controller 301 issues an instruction for performing radiography to the radiation control device 120. By this, the radiography is performed, and radiation transmitted through the subject H is obtained as the radiographic image 500 by the radiation detection unit 150.

In step S402, the image obtaining unit 302 obtains the radiographic image 500 obtained by the radiation detection unit 150 through the input/output unit 208. Thereafter, in step S403, the image processing unit 303 performs image processing, such as gradation conversion, on the radiographic image 500 and specifies an irradiation field region in the radiographic image 500. In the example of FIG. 5, the image processing unit 303 specifies an irradiation field region 510 included in the radiographic image 500. Here, the irradiation field region 510 is a rectangular region. The image obtaining unit 302 stores the radiographic image 500 and irradiation field region information indicating the irradiation field region 510 in the image processing unit 303.

In step S404, the rotation calculation unit 305 calculates a rotation angle of the irradiation field region 510. Specifically, first, the rotation calculation unit 305 obtains coordinates of each of the four points including an uppermost end point, a lowermost end point, a rightmost end point, and a leftmost end point of the irradiation field region 510 having the rectangular shape. Here, the size of the radiographic image 500 corresponds to 2800×3408 pixels in lateral and longitudinal directions (X and Y directions) and a lower left of the radiographic image 500 is set as an origin (0, 0). It is assumed that coordinates of four apices described below are specified in the irradiation field region 510 of FIG. 5.

Uppermost End Point A: (X, Y)=(1400, 3067)

Lowermost End Point B: (X, Y)=(1120, 1022)
Leftmost End Point C: (X, Y)=(280, 2836)
Rightmost End Point D: (X, Y)=(2240, 1704)

In this case, first, the rotation calculation unit 305 focuses on the two points, that is, the lowermost end point B and the rightmost end point D, and calculates a difference between X coordinates of the rightmost end point D and the lowermost end point B and a difference between Y coordinates of the rightmost end point D and the lowermost end point B. The rotation calculation unit 305 obtains an inclination angle in a top-bottom direction of the irradiation field region 510 relative to a top-bottom direction of the radiographic image 500 using the difference between the X coordinates and the difference between the Y coordinates by means of a trigonometric function, and calculates a rotation angle based on the inclination angle. The process in step S404 is an example of a determination process of determining a rotation angle.

In the example of FIG. 5, the difference between the X coordinates is 1120 according to Expression 1, and the difference between the Y coordinates is 682 according to Expression 2. Furthermore, the inclination angle of 31 degrees is obtained in accordance with the trigonometric function. By this, it is determined that the irradiation field region 510 has been rotated by 31 degrees in a counterclockwise direction relative to the radiographic image 500. Accordingly, in this case, the rotation calculation unit 305 obtains a rotation angle of 31 degrees in a clockwise direction.

$$2240-1120=1120 \qquad \text{Expression 1}$$

$$1704-1022=682 \qquad \text{Expression 2}$$

In step S405, the geometric transform unit 306 determines whether the irradiation field region 510 is inclined relative to the radiographic image 500. When the geometric transform unit 306 determines that the irradiation field region 510 is inclined (YES in step S405), the process proceeds to step S406. When the geometric transform unit 306 determines that the irradiation field region 510 is not inclined (NO in step S405), the process proceeds to step S407.

Figure 6:
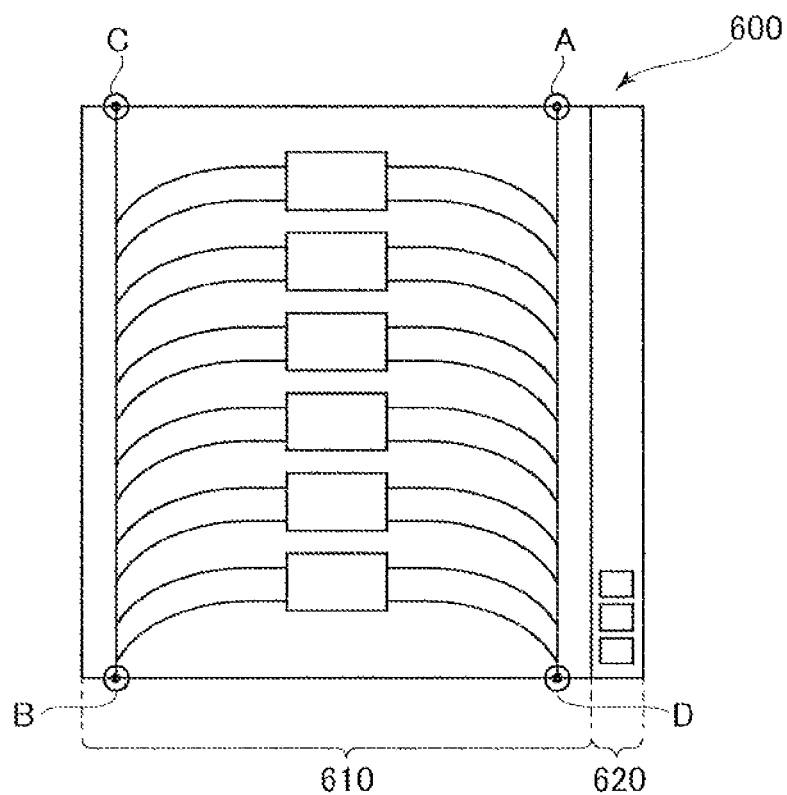
FIG. 6 is a diagram illustrating a display region.

In step S406, the geometric transform unit 306 rotates the radiographic image 500 by the rotation angle. By this, the top-bottom direction of the irradiation field region 510 coincides with the top-bottom direction of the display unit 205. Specifically, the irradiation field region 510 may be displayed in an erected state. Thereafter, in step S407, the geometric transform unit 306 enlarges or reduces the radiographic image 500 in size such that one of an upper side, a lower side, a left side, and a right side of the irradiation field region 510 coincides with a corresponding one of four sides of a display region of a rectangular shape. The display region indicates a region in which the radiographic image 500 is displayed in the display unit 205. FIG. 6 is a diagram illustrating a display region. A display region 610 is displayed in a left portion in a display screen 600 displayed in the display unit 205. An operation region 620 is also formed in the display screen 600, and operation buttons are displayed in the operation region 620. The geometric transform unit 306 also stores in the storage unit 304 the radiographic image 500 that has been subjected to the geometric processing, that is, the radiographic image 500 that has been subjected to the rotation and the magnification change.

Note that, when the irradiation filed region 510 is not inclined (NO in step S405), the geometric transform unit 306 enlarges or reduces the radiographic image 500 in size such that all of an uppermost end point, a lowermost end point, a leftmost end point, and a rightmost end point are included in the display region in step S407. The process in step S407 is an example of the magnification change processing. After the process in step S407, the display controller 307 causes the display unit 205 to display the radiographic image 500 that has been processed by the geometric transform unit 306 in step S408. The process in step S408 is an example of display processing.

The magnification change processing will be described in detail. A longitudinal length and a lateral length of the irradiation field region 510 may be calculated using the coordinates of each of the end points and the trigonometric function. The lateral length is 1311 according to the coordinates of the rightmost end point D and the lowermost end point B. Furthermore, the longitudinal length is 1999 according to the coordinates of the leftmost end point C and the lowermost end point B.

When the display region 610 has 1600×1200 pixels in the longitudinal and lateral directions (Y and X directions), the geometric transform unit 306 reduces the size of the radiographic image 500 so that the entire irradiation field region 510 is included in the display region 610. In this concrete example, a reduction ratio in the longitudinal direction is 80% according to Expression 3, and a reduction ratio in the lateral direction is 91% according to Expression 4.

$$(1600/1999)\times 100=80\% \qquad \text{Expression 3}$$

$$(1200/1311)\times 100=91\% \qquad \text{Expression 4}$$

The geometric transform unit 306 reduces the size of the radiographic image 500 using the reduction ratio of 80%, in the reduction ratios in the longitudinal and lateral directions, for obtaining a smaller radiographic image 500. By this, the leftmost end point C and the lowermost end point B of the irradiation field region 510 coincides with a longitudinal direction of the display region 610.

As described above, in the radiographic system 100 of the first embodiment, the geometric processing is performed so that the irradiation field region 510 erects relative to the display unit 205 and the irradiation field region 510 is displayed in the display unit 205 in an appropriate size. Accordingly, the imaging control device 110 may appropriately display the image including the irradiation field region 510.

Note that, as a modification example, the rotation calculation unit 305 may calculate an orientation of the subject in the irradiation field region by performing image analysis on the irradiation field region and calculate a rotation angle, by taking an inclination of the subject relative to the X-ray detector into consideration, so that the subject erects in the irradiation field region.

Second Embodiment

Next, a radiographic system 100 according to a second embodiment will be described, in which portions different from the radiographic system 100 according to the first embodiment are mainly described. In the radiographic system 100 of the second embodiment, a method for calculating a rotation angle employed in an imaging control device 110 is different from the method in the first embodiment. Hereinafter, a process of calculating a rotation angle performed by a rotation calculation unit 305 of the imaging control device 110 according to the second embodiment will be described.

The rotation calculation unit 305 of the second embodiment calculates a rotation angle such that a ratio of an irradiation field region in a display region 610 becomes largest based on the irradiation field information stored in a storage unit 304. A process performed by the rotation calculation unit 305 will be described in detail. Note that coordinates in the irradiation field region are described below.

Uppermost End Point A: (X, Y)=(1869, 3292)
Lowermost End Point B: (X, Y)=(1120, 1022)
Leftmost End Point C: (X, Y)=(603, 2952)
Rightmost End Point D: (X, Y)=(2386, 1362)

First, the rotation calculation unit 305 calculates a difference between Y coordinates of the uppermost end point A and the lowermost end point B in the irradiation field region. Subsequently, the rotation calculation unit 305 calculates a difference between X coordinates of the leftmost end point C and the rightmost end point D. A difference between Y coordinates of the uppermost end point A and the lowermost end point B is 2270 according to Expression 5. A difference between X coordinates of the leftmost end point C and the rightmost end point D is 1783 according to Expression 6.

$$3292-1022=2270 \qquad \text{Expression 5}$$

$$2386-603=1783 \qquad \text{Expression 6}$$

Subsequently, the rotation calculation unit 305 obtains a rectangular region that has the individual difference values as a longitudinal length and a lateral length and that includes all the uppermost end point A, the leftmost end point C, the lowermost end point B, and the rightmost end point D. Thereafter, the rotation calculation unit 305 obtains a magnification varying ratio for displaying the entire rectangular region including the irradiation field region in the display region 610. In the example described above, a magnification varying ratio in the longitudinal direction is 70% according to Expression 7, and a magnification varying ratio in the lateral direction is 67% according to Expression 8. In the two magnification varying ratios, the magnification varying ratio of 70% attains a larger radiographic image, and therefore, a size reduction ratio at a rotation angle of 0 degrees is calculated to be 70%.

$$(1600/2270) \times 100 = 70\% \qquad \text{Expression 7}$$

$$(1200/1783) \times 100 = 67\% \qquad \text{Expression 8}$$

Subsequently, the rotation calculation unit 305 rotates the radiographic image in a counterclockwise direction by 1 degree with a center point of the radiographic image at a center. By this, the coordinates of each of the uppermost end point A, the lowermost end point B, the leftmost end point C, and the rightmost end point D of the irradiation field region also shift with the center point of the radiographic image at the center. Coordinates after the shift of each of the points with the center point of the radiographic image at the center may be calculated using an equation of the affine transformation. The rotation calculation unit 305 obtains, as with the case of the angle of 0 degrees, a rectangular region including all of an uppermost end point A', a lowermost end point B', a leftmost end point C', and a rightmost end point D' in accordance with the coordinates of the calculated uppermost end point A', the calculated lowermost end point B', the calculated leftmost end point C', and the calculated rightmost end point D'. The rotation calculation unit 305 obtains a magnification varying ratio that enables the obtained entire rectangular region to be included in the display region 610 as a size reduction ratio for the rotation angle of 1 degree.

The rotation calculation unit 305 compares the size reduction ratio at the rotation angle of 1 degree and the size reduction ratio at the rotation angle of 0 degrees with each other and selects one of the rotation angles that corresponds to a size reduction ratio that attains a larger irradiation field region. The rotation calculation unit 305 calculates a rotation angle for maximizing a display ratio of the irradiation field region by repeatedly performing the same process in a range from a rotation angle of 2 degrees to a rotation angle of 359 degrees. In this case also, the geometric transform unit 306 rotates the radiographic image by the rotation angle calculated by the rotation calculation unit 305. Note that other configurations and other processes of the radiographic system 100 according to the second embodiment are the same as those of the radiographic system 100 according to the first embodiment.

Third Embodiment

Next, a radiographic system 100 according to a third embodiment will be described, in which portions different from the radiographic systems 100 according to the foregoing embodiments are mainly described. In the radiographic system 100 according to the third embodiment, a geometric transform unit 306 of an imaging control device 110 controls a determination as to whether rotation is to be performed in accordance with deterioration of image quality caused when a radiographic image is rotated. A storage unit 304 stores in advance a deterioration ratio table illustrating deterioration ratios based on rotation angles at times when the radiographic image is rotated. If the image is rotated, pixel interpolation is required, and therefore, image quality is deteriorated. Furthermore, a proportion of the pixel interpolation required affects a rotation angle. Therefore, image quality deterioration ratios for individual rotation angles may be defined in advance. The deterioration ratio table includes information in which a rotation angle and a deterioration ratio are associated with each other. FIG. 7 is an example of a deterioration ratio table 700. According to the deterioration ratio table 700, when the rotation angle is 15 degrees, the image quality deterioration ratio is 2.5% and when the rotation angle is 31 degrees, the image quality deterioration ratio is 1.9%, for example. Note that, although an image quality deterioration ratio is specified relative to a specific angle in the example of FIG. 7, the image quality deterioration ratio varies in accordance with an algorithm of image display in practice.

Furthermore, the storage unit 304 stores a threshold value of the deterioration ratio. Note that the storage unit 304 may store different threshold values for different portions. Furthermore, the storage unit 304 may store a plurality of threshold values for determining deterioration stepwise.

Figure 8:
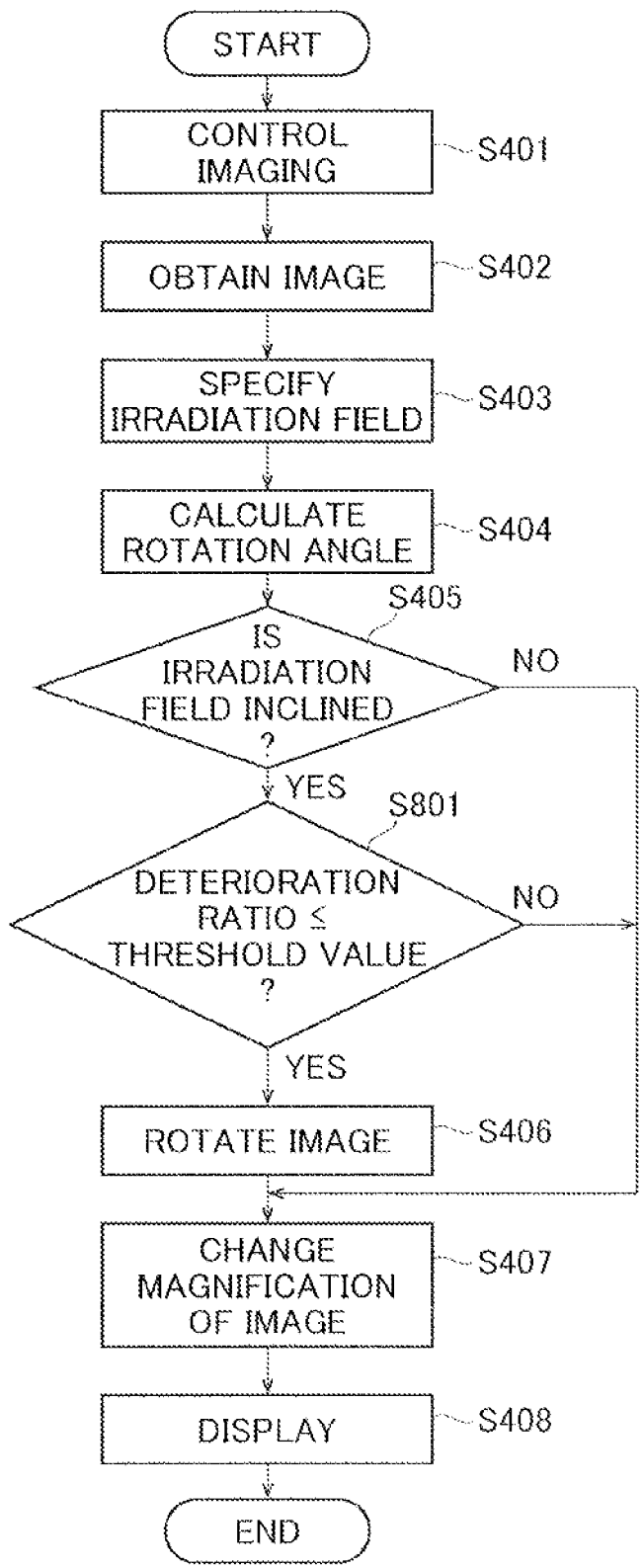
FIG. 8 is a flowchart of the radiographic image processing.

FIG. 8 is a flowchart of radiographic image processing according to the third embodiment. Note that, in processes of the radiographic image processing illustrated in FIG. 8, processes the same as those of the radiographic image processing according to the first embodiment described with reference to FIG. 4 are denoted by reference numerals the same as those in FIG. 4. In step S405, when the geometric transform unit 306 determines that the irradiation field region is inclined (YES in step S405), the process proceeds to step S801.

In step S801, the geometric transform unit 306 specifies a deterioration ratio in accordance with a rotation angle calculated in step S404 with reference to the deterioration ratio table 700. The geometric transform unit 306 compares the specified deterioration ratio with the threshold value. When the geometric transform unit 306 determines that the deterioration ratio is equal to or smaller than the threshold value (YES in step S801), the process proceeds to step S406. When the geometric transform unit 306 determines that the deterioration ratio is larger than the threshold value (NO in step S801), the process proceeds to step S407 without performing the rotation process.

It is assumed that a rotation angle θ is 31 degrees similarly to the example described with reference to FIG. 5. In this case, it is determined that the deterioration ratio is 1.9% according to the deterioration ratio table 700. In a case where the threshold value of the deterioration ratio is 2%, when the rotation angle θ is 31 degrees, the deterioration ratio is smaller than the threshold value, and therefore, rotation is executed by the rotation angle θ of 31 degrees.

Furthermore, an irradiation field region defined by the following points will be described as an example.
Uppermost End Point E: (X, Y)=(1869, 3292)
Lowermost End Point F: (X, Y)=(1120, 1022)
Leftmost End Point G: (X, Y)=(603, 2952)
Rightmost End Point H: (X, Y)=(2386, 1362)

In this case, a difference between X coordinates of the lowermost end point F and the rightmost end point H is 1266 according to Expression 9, and a difference between Y coordinates of the lowermost end point F and the rightmost end point H is 340 according to Expression 10. Accordingly, a rotation angle θ of 15 degrees is obtained by a trigonometric function. In this case, the deterioration ratio is 2.5% that is larger than the threshold value 2% according to the deterioration ratio table 700 in FIG. 7. Therefore, control is performed such that rotation for the rotation angle θ of 15 degrees is not executed.

$$2386-1120=1266 \qquad \text{Expression 9}$$

$$1362-1022=340 \qquad \text{Expression 10}$$

Figure 9:
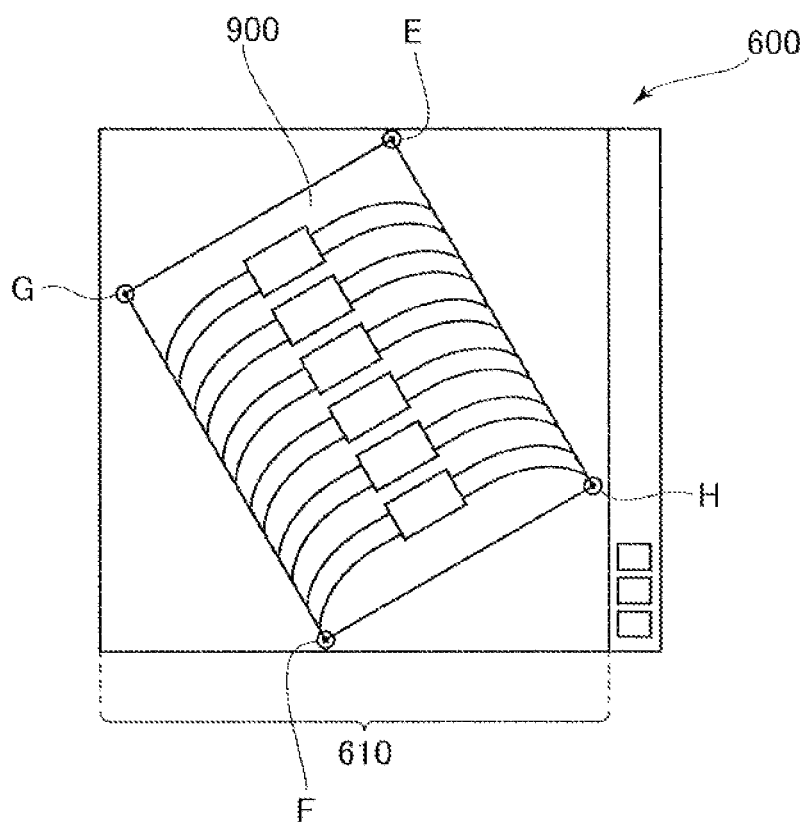
FIG. 9 is a diagram illustrating an example of display of an irradiation field region.

FIG. 9 is a diagram illustrating an example of display of an irradiation field region 900 in the case where the rotation is not performed. When the rotation for the angle θ of 15 degrees is not executed in the example described above, in step S407, the geometric transform unit 306 calculates a difference between Y coordinates of an uppermost end point E and a lowermost end point F of the irradiation field region 900. The geometric transform unit 306 also calculates a difference between X coordinates of a leftmost end point G and a rightmost end point H. The difference between the Y coordinates of the uppermost end point E and the lowermost end point F is 2270 according to Expression 11. Furthermore, the difference between the X coordinates of the leftmost end point G and the rightmost end point H is 1783 according to Expression 12.

$$3292-1022=2270 \qquad \text{Expression 11}$$

$$2386-603=1783 \qquad \text{Expression 12}$$

Next, the geometric transform unit 306 obtains a rectangular region that has the individual difference values as a longitudinal length and a lateral length and that includes all the uppermost end point E, the leftmost end point G, the lowermost end point F, and the rightmost end point H. In the example, a magnification varying ratio in the longitudinal direction is 70% according to Expression 13, and a magnification varying ratio in the lateral direction is 67% according to Expression 14. Note that a display size of a display region 610 corresponds to 1600×1200 pixels in the longitudinal and lateral directions. In this case, the geometric transform unit 306 reduces the size of the radiographic image such that the uppermost end point E and the lowermost end point F of the irradiation field region are in contact with sides of the display region 610.

$$(1600/2270)\times 100=70\% \qquad \text{Expression 13}$$

$$(1200/1783)\times 100=67\% \qquad \text{Expression 14}$$

Note that other configurations and other processes of the radiographic system 100 according to the third embodiment are the same as those of the radiographic systems 100 according to the foregoing embodiments. As described above, according to the third embodiment, the imaging control device 110 may control rotation in accordance with deterioration of image quality based on the rotation of an image.

Fourth Embodiment

Next, a radiographic system 100 according to a fourth embodiment will be described, in which portions different from the radiographic systems 100 according to the foregoing embodiments are mainly described. The radiographic system 100 according to the fourth embodiment may selectively display a radiographic image obtained after geometric processing or a radiographic image that has not been subjected to the geometric processing. In the fourth embodiment, a geometric transform unit 306 of an imaging control device 110 copies a radiographic image stored in a storage unit 304, performs the geometric processing on the copied image, and stores in the storage unit 304 the copied image that has been subjected to the geometric processing.

Figure 10:
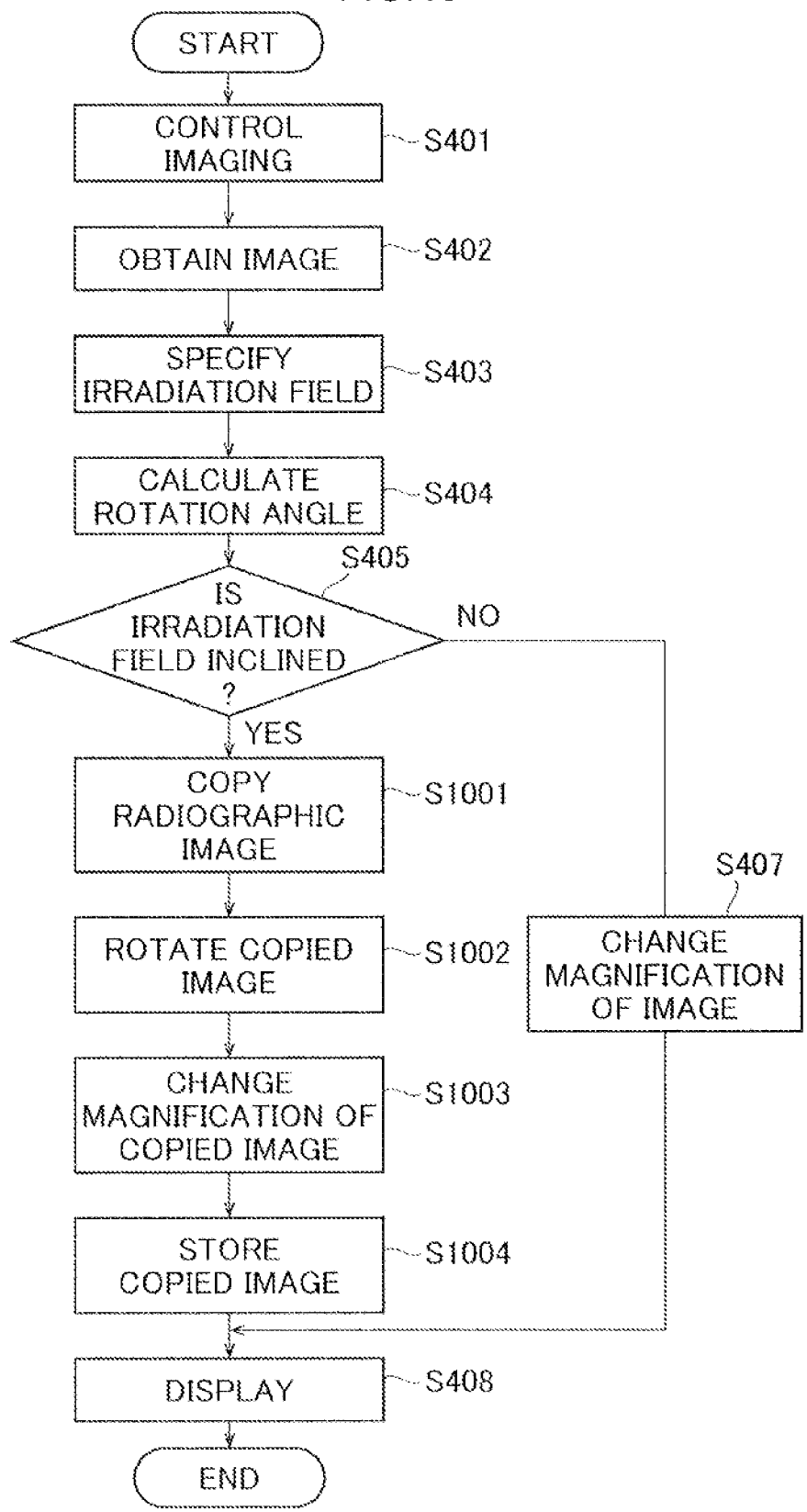
FIG. 10 is a flowchart of radiographic image processing.

FIG. 10 is a flowchart of radiographic image processing according to the fourth embodiment. Note that, in processes of the radiographic image processing illustrated in FIG. 10, the same processes as those of the radiographic image processing according to the first embodiment described with reference to FIG. 4 are denoted by the same reference numerals as those in FIG. 4. In step S405, when the geometric transform unit 306 determines that an irradiation field region is inclined (YES in step S405), the process proceeds to step S1001.

In step S1001, the geometric transform unit 306 copies a radiographic image stored in the storage unit 304. In step S1002, the geometric transform unit 306 performs rotation processing on the copied image. This process is the same as the process in step S406 (FIG. 4) described in the first embodiment. In step S1003, the geometric transform unit 306 performs magnification varying processing on the copied image. This process is the same as the process in step S407 (FIG. 4). In step S1004, the geometric transform unit 306 stores in the storage unit 304 the copied image that has been subjected to the geometric processing, and the process proceeds to step S408. In step S408, a display controller 307 controls display of the copied image that has been subjected to the geometric processing.

After the copied image is stored in the storage unit 304 by the radiographic image processing, the display controller 307 may display the copied image and a radiographic image that has not been subjected to the rotation processing in a display unit 205. The display controller 307 displays at least one of the copied image and the radiographic image in the display unit 205 in accordance with a user operation received through the operation unit 206, for example.

In a case where two or more radiographic images are captured in the same examination, when different radiographic images are switched to be displayed, a display state immediately after the image capturing may be desired to be checked in some cases. In such a case, when receiving from the operation unit 206 an instruction for displaying the copied image that has been rotated, the display controller 307 performs control such that the copied image is displayed.

On the other hand, when checking whether a required diagnosis portion is entirely included in the irradiation field region in the radiographic image, a region other than the irradiation field region may be desired to check in some cases. In such a case, it is assumed that an instruction for performing check on the region other than the irradiation field region is received when a control button for image check included in the operation unit 206 is pressed. In this case, the display controller 307 performs control such that a radiographic image that has not been subjected to the rotation processing is displayed.

Note that switching between display of one radiographic image and display of another radiographic image is not only performed by the user operation but also performed based on a setting of the system. Note that other configurations and other processes of the radiographic system 100 according to the fourth embodiment are the same as those of the radiographic systems 100 according to the foregoing embodiments.

In this way, according to the fourth embodiment, the imaging control device 110 may selectively display an image that has been subjected to the rotation processing or an image that has not been subjected to the rotation processing.

Fifth Embodiment

Next, a radiographic system 100 according to a fifth embodiment will be described, in which portions different from the radiographic systems 100 according to the foregoing embodiments are mainly described. The radiographic system 100 according to the fifth embodiment may selectively output to an external apparatus an image that has been subjected to geometric processing or an image that has not been subjected to the geometric processing. In the fifth embodiment, a geometric transform unit 306 of an imaging control device 110 copies a radiographic image stored in a storage unit 304, performs the geometric processing on the copied image, and stores in the storage unit 304 the copied image that has been subjected to the geometric processing. The geometric transform unit 306 also stores geometric information in the storage unit 304. Here, the geometric information indicates the geometric processing performed on the copied image and includes a rotation angle, a magnification varying ratio, and the like.

FIG. 11 is a flowchart of radiographic image processing according to the fifth embodiment. Note that, in processes of the radiographic image processing illustrated in FIG. 11, the same processes as those of the radiographic image processing according to the first embodiment described with reference to FIG. 4 are denoted by the same reference numerals as those in FIG. 4. After the process in step S407, the geometric transform unit 306 stores geometric information in the storage unit 304 in step S1101, and the process proceeds to step S408.

After the geometric information is stored in the storage unit 304 by the radiographic image processing, a CPU 201 may transmit to an external apparatus the radiographic image that has been subjected to the geometric processing using the geometric information in addition to the radiographic image that has not been subjected to the geometric processing. The CPU 201 selectively transmits one of the radiographic images to the external apparatus in accordance with a user operation, for example.

Examples of a standard defined by Integrating the Healthcare Enterprise (IHE) for transmitting an image to an external apparatus include consistent presentation of images (CPI). In this standard, consistency of a display state independent from an apparatus is required to be provided. In this case, when an image outputting instruction is received by pressing a control button, in the operation unit 206, for instructing the CPU 201 of an output based on the CPI, for example, the CPU 201 transmits to the external apparatus the radiographic image that has not been subjected to the geometric processing.

On the other hand, there is a case, which is not based on the CPI, where a similar display state to the display state in the display unit 205 is desired to be displayed also in the external apparatus. In this case, it is assumed that a control button, in the operation unit 206, for instructing the CPU 201 of an output not based on the CPI has been pressed. In this case, the CPU 201 performs the geometric processing on the radiographic image using the geometric information and transmits the processed image to the external apparatus. Note that other configurations and other processes of the radiographic system 100 according to the fifth embodiment are the same as those of the radiographic systems 100 according to the foregoing embodiments.

According to the foregoing embodiments, an image including an irradiation field region can be appropriately displayed.

Other Embodiments

Embodiments can also be realized by a computer of a system or apparatus that reads out and executes computer executable instructions (e.g., one or more programs) recorded on a storage medium (that may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-074012, filed Apr. 6, 2018, which is hereby incorporated by reference herein in its entirety.

What is claimed is:

1. A radiographic image processing apparatus, comprising:
at least one memory storing instructions; and
at least one processor that, when executing the instructions, causes the radiographic image processing apparatus to:
specify an irradiation field region in a radiographic image;
determine, based on the irradiation field region, a rotation angle of the radiographic image;
rotate, based on the determined rotation angle, the radiographic image; and
perform control to display a rotated radiographic image on a display unit.

2. The radiographic image processing apparatus according to claim 1, wherein the at least one processor, when executing the instructions, further causes the radiographic image processing apparatus to:
change, based on a size of the display unit, a magnification of the radiographic image, and
perform control to display the radiographic image subjected to the magnification change.

3. The radiographic image processing apparatus according to claim 2, wherein the at least one processor, when executing the instructions, further causes the radiographic image processing apparatus to:
store, in a storage device, the radiographic image subjected to the rotation and the magnification change.

4. The radiographic image processing apparatus according to claim 2, wherein the at least one processor, when executing the instructions, further causes the radiographic image processing apparatus to:
store, in a storage device, the rotation angle and a magnification varying ratio of the magnification.

5. The radiographic image processing apparatus according to claim 1, wherein the at least one processor, when executing the instructions, determines the rotation angle based on a geometric relationship between the irradiation field region and the radiographic image.

6. The radiographic image processing apparatus according to claim 5, wherein the at least one processor, when executing the instructions, determines the rotation angle based on an inclination of the irradiation field region relative to the radiographic image.

7. The radiographic image processing apparatus according to claim 5, wherein the at least one processor, when executing the instructions, determines a first rotation angle as the rotation angle, the first rotation angle being with which a top-bottom direction of the irradiation field region coincides with a top-bottom direction of the display unit.

8. The radiographic image processing apparatus according to claim 1, wherein
the irradiation field region is a rectangular region, and
the at least one processor, when executing the instructions, determines the rotation angle based on positions of four apices of the irradiation field region.

9. The radiographic image processing apparatus according to claim 1, wherein the at least one processor, when executing the instructions, determines the rotation angle of the radiographic image based on a magnification varying ratio of the radiographic image, to display the irradiation field region in the display unit.

10. The radiographic image processing apparatus according to claim 1, wherein the at least one processor, when executing the instructions, determines the rotation angle based on an image of the irradiation field region.

11. The radiographic image processing apparatus according to claim 1, wherein the at least one processor, when executing the instructions, controls rotation based on deterioration of image quality of the radiographic image based on the rotation angle.

12. The radiographic image processing apparatus according to claim 1, further comprising:
a storage device configured to store a table indicating a rotation angle and a deterioration ratio of the radiographic image,
wherein the at least one processor, when executing the instructions, rotates the radiographic image when the deterioration ratio corresponding to a determined rotation angle is less than or equal to a threshold value.

13. A radiographic image processing method of a radiographic image processing apparatus, the radiographic image processing method comprising:
specifying an irradiation field region in a radiographic image;
determining, based on the irradiation field region, a rotation angle of the radiographic image;
rotating, based on the determined rotation angle, the radiographic image; and
performing control to display a rotated radiographic image on a display unit.

14. The radiographic image processing method according to claim 13, further comprising:
changing, based on a size of the display unit, a magnification of the radiographic image,
wherein the performing includes performing control to display the radiographic image subjected to the magnification change.

15. The radiographic image processing method according to claim 13, wherein
the determining includes determining the rotation angle based on a geometric relationship between the irradiation field region and the radiographic image.

16. The radiographic image processing method according to claim 13, wherein
the determining includes determining the rotation angle based on an image of the irradiation field region.

17. A non-transitory computer-readable storage medium storing a program for causing a computer to execute a radiographic image processing method, the radiographic image processing method comprising:
specifying an irradiation field region in a radiographic image;
determining, based on the irradiation field region, a rotation angle of the radiographic image;
rotating, based on the determined rotation angle, the radiographic image; and
performing control to display a rotated radiographic image on a display unit.

18. The non-transitory computer-readable storage medium according to claim 17, the radiographic image processing method further comprising:
changing, based on a size of the display unit, a magnification of the radiographic image,
wherein the performing includes performing control to display the radiographic image subjected to the magnification change.

19. The non-transitory computer-readable storage medium according to claim 17, wherein the determining includes determining the rotation angle based on a geometric relationship between the irradiation field region and the radiographic image.

20. The non-transitory computer-readable storage medium according to claim 17, wherein
the determining includes determining the rotation angle based on an image of the irradiation field region.

* * * * *